(12) United States Patent
Yagi et al.

(10) Patent No.: US 6,313,194 B1
(45) Date of Patent: Nov. 6, 2001

(54) DEGRADING METHOD OF POLYMER

(75) Inventors: Tadashi Yagi; Kazuto Ishihara, both of Mobara; Takeshi Irimajiri, Tokyo, all of (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 08/725,506

(22) Filed: Oct. 4, 1996

Related U.S. Application Data

(63) Continuation of application No. PCT/JP96/00448, filed on Feb. 27, 1996, now abandoned.

(30) Foreign Application Priority Data

Feb. 28, 1995 (JP) .................................................... 7-040240

(51) Int. Cl.⁷ ...................................................... C08K 5/00
(52) U.S. Cl. ........................... 523/124; 523/125; 523/128
(58) Field of Search .................................... 523/124, 125, 523/128

(56) References Cited

U.S. PATENT DOCUMENTS 5,378,738 * 1/1995 Deguchi et al. ..................... 435/262

OTHER PUBLICATIONS

Patent Abstracts of Japan, vol. 18, No. 185 (C–1185), Mar. 30, 1994 & JP 05344897A, (Amano Pharmaceut. Co. Ltd.), Dec. 27, 1993 *abstract*.

Patent Abstracts of Japan, vol. 005, No. 067 (C–053), May 7, 1981, & JP 56018587 A (Tottori Daigaku), Feb. 21, 1981 *abstract*.

Patent Abstracts of Japan, vol. 095, No. 002, Mar. 31, 1995 & JP 06319533A (Sumitomo Metal Ind., Ltd.), Nov. 22, 1994 *abstract*.

* cited by examiner

*Primary Examiner*—Edward J. Cain
(74) *Attorney, Agent, or Firm*—Burns, Doane, Swecker & Mathis, L.L.P.

(57) ABSTRACT

A method for degrading a polymer by bringing same into contact with a solid phase composed of a carrier, a microorganism and an aqueous solution. The aqueous solution contains nutrients required for the growth of the microorganism and water. The carrier has a maximum water retention of at least 40 wt. % but at most 4,000 wt. %, the aqueous solution is retained in the carrier in an amount of at least 10% but at most 100% of the maximum water retention of the carrier, and the solid phase has a percentage of interstices of 25% or greater but smaller than 100%.

19 Claims, 1 Drawing Sheet

DEGRADING METHOD OF POLYMER

CROSS REFERENCE TO RELATED APPLICATIONS

This application is a continuation of International Application PCT/JP96/00448, with an International filing date of Feb. 27, 1996, which designated the U.S., now abandoned

TECHNICAL FIELD

This invention relates to a method for degrading a polymer, especially a polymer having biodegradability with a microorganism and also to an apparatus suitable for use in the practice of the method.

BACKGROUND ART

High molecular compounds typified by plastics are abundantly produced and used around the world in a wide variety of fields for their convenient properties of lightness and strength.

However, used high molecular compounds generally do not degrade in the natural environment. Even if they are buried, they remain undegraded and accumulate year after year in the global environment. On the other hand, incineration of high molecular compounds causes problems such as occurrence of high heat and toxic gas. Accordingly, disposal of high molecular compounds has now turned to be a social problem.

Reflecting the ever-increasing public concern over environmental problems on the global scale in recent years, a great deal of research is now under way on biodegradable high-molecular substances which can be degraded by a microorganism in the natural environment and also on degradation of hardly-biodegradable polymers under the action of an enzyme or a microorganism. Some of this research is finding practical utility.

Biodegradable high-molecular substances which are now under research can be divided roughly into "synthetic high-molecular substances", "microbially-produced high-molecular substances" and "plant-or animal-derived, natural high-molecular substances".

Synthetic high-molecular substances permit molecular designing of high molecular substances having various functions from a large number of structural units and are expected to become substitutes for general plastics.

As a result of screening of polymer-degrading microorganisms, it has been found that water-soluble polyvinyl alcohol and polyethylene glycol can be degraded by certain microorganisms. Polyvinyl alcohol is degradable by a bacterium belonging to the genus of Pseudomonas (Suzuki et al., Agric. Biol. Chem., 37, 747, 1973). Further, polyethylene glycol whose molecular weight is 6,000 is degradable by a symbiotic bacterium system of a Pseudomonas sp. and a Flavobacterium Sp. (Kawai et al., J. Ferment. Technol., 55, 125, 1977). It has also been reported that water-insoluble solid aliphatic polyesters, especially hardly-degradable polycaprolactones are hydrolyzed in soil (Potts et al., Polym. Prepr., 13, 629, 1972).

Among aliphatic polyesters known as biodegradable high-molecular substances, polymers which are formed from lactic acid, glycolic acid, or lactic acid and glycolic acid have the features that they are more mold-resistant than natural high-molecular substances derived from plants or animals and also that they are superior in transparency to microbially-produced high-molecular substances and other synthetic high-molecular substances. Moreover, as the polymers formed from lactic acid, glycolic acid, or lactic acid and glycolic acid are hydrolyzed into lactic acid or glycolic acid, they have high biosafety and are thus suited for use in the field of medical materials or foods.

Properties required for a biodegradable high-molecular substance are high material strength during use but prompt degradation in the environment after disposal. Polymers formed from lactic acid, glycolic acid, or lactic acid and glycolic acid are known to be non-enzymatically hydrolyzable in the living body [Yamane et al., Jinko Zoki (Artificial Organs), 15, 1751, 1986]. However, their hydrolyzability decreases with the molecular weight. On the other hand, the material strength increases with the molecular weight. Accordingly, these properties contradict each other.

For example, poly(L-lactic acid) degrades in about 2 weeks in physiological saline when its molecular weight is 1,000. Its material strength is however so low that it is not practically usable. When the molecular weight increases to 10,000 or higher, its material strength increases to such a level as permitting its use as plastics although it becomes hardly degradable.

Several methods are known for the degradation of polymers formed from lactic acid, glycolic acid, or lactic acid and glycolic acid and having sufficient material strength. For example, it has been reported that the degradation speed of polylactic acid having a molecular weight of about 100,000 becomes higher when the polylactic acid is added with nutrients for a microorganism and is then buried in the earth (Japanese Patent Application Laid-Open No. 168150/1992). Even by this method, however, it takes about 3 months until the polymer degrades completely.

As a still further method for degrading a biodegradable high-molecular substance, it is also known that the biodegradable high-molecular substance may degrade when it is placed in a compost formed of sewage sludge, urban garbage, livestock excrements and the like. However, a compost is formed of various components and its form and colonies substantially vary depending on the place and also season in which the compost is produced. Therefore the method making use of a conventional compost cannot surely degrade a biodegradable high-molecular substance with good reproducibility, and in some instances, the biodegradable high-molecular substance may remain practically undegraded.

As has been described above, some examples are known to date regarding methods for degrading polymers by microorganisms. However, they are all accompanied by problems such as the need for a long time for the degradation of polymers and lack of reproducibility of degradation, so that they are not suited for industrial applications.

With the above-described conventional art in view, an object of the present invention is to provide a method for degrading a polymer having high strength at a time of use, which makes use of a solid phase with a microorganism, nutrients required for the growth of the microorganism and water retained on a carrier for promptly degrading the polymer with good reproducibility, and also an apparatus suitable for use in the practice of the method.

DISCLOSURE OF THE INVENTION

Under the above-described circumstances, the present inventors have proceeded with an extensive investigation. As a result, it has been found that concerning degradation of a polymer by a microorganism, use of a solid phase—which has been formed by causing a carrier, which is selected from carriers having ability to retain the microorganism, nutrients and water and has a predetermined maximum water retention, to retain the microorganism, the nutrients and water to control its percentage of interstices within a predetermined range—allows the degradation of the polymer by the microorganism to promptly take place. Based on this finding, the present invention has been completed.

Namely, the present invention provides a method for degrading a polymer by bringing the polymer into contact with a solid phase composed of a carrier, a microorganism and an aqueous solution, said aqueous solution containing nutrients required for the growth of the microorganism and water, wherein said carrier has a maximum water retention of at least 40 wt. % but at most 4,000 wt. %, said aqueous solution is retained in said carrier in an amount of at least 10% but at most 100% of said maximum water retention of said carrier, and said solid phase has a percentage of interstices of 25% or greater but smaller than 100%; and also an apparatus suitable for use in the practice of the method.

BRIEF DESCRIPTION OF THE DRAWINGS

FIGS. 1 and 2 illustrate a polymer degradation apparatus useful in the practice of the present invention, in which FIG. 1 shows a side cross-section and FIG. 2 is a front cross-section.

BEST MODE FOR CARRYING OUT THE INVENTION

Figure 1:
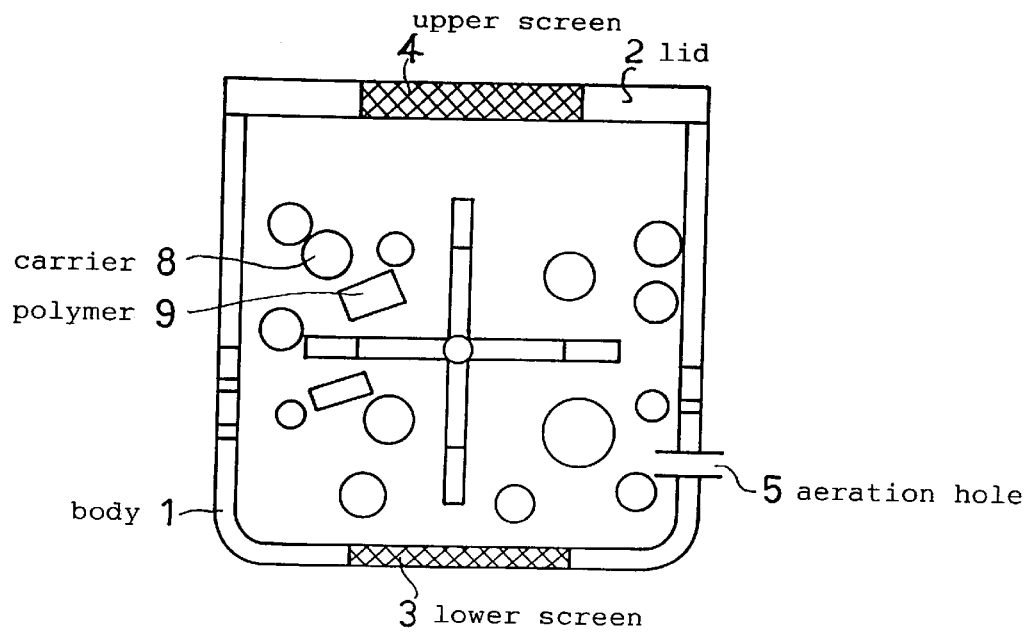

The carrier, which is used in the present invention to retain the microorganism and the nutrients, is required to be of such quality as not inhibiting growth of the microorganism, to permit the retention of the nutrients and water required for the growth of the microorganism and, when employed as a solid phase in the method of the present invention, to enable formation of interstices to such a degree as permitting a supply of oxygen required for the growth of the microorganism from the air. The maximum water retention of the carrier, which meets such requirements, is at least 40 wt. % (gram-water/gram-dry carrier) but at most 4,000 wt. % (gram-water/gram-dry carrier), preferably at least 50 wt. % (gram-water/gram-dry carrier) but at most 3,000 wt. % (gram-water/gram-dry carrier).

The carrier employed in the present invention is made of an organic high-molecular substance or an inorganic substance.

Illustrative of the organic high-molecular substance are non-human animal materials, such as leather and wool, and their processed products; plant materials, such as saw dust, loofahs, husks, millets, wheat bran, paper and cotton, and their processed products; foamed organic high-molecular substances such as porous foamed cellulose, foamed urethane and foamed polyvinyl alcohol; and fibrous organic high-molecular substances such as non-woven fabrics. Further, foamed organic substances which are biodegradable high-molecular substances by themselves can also be mentioned as examples.

On the other hand, illustrative of the inorganic substance are molecular sieve, vermiculite, perlite, stainless steel fibers, aluminum wool, glass wool, and aluminum honeycomb cones.

Substances other than those exemplified above are also usable as carriers in the present invention insofar as they can satisfy the requirement of the maximum water retention. The above-exemplified carriers are usable either singly or in combination in the present invention, with the proviso that, when the carrier is a mixture of plural substances, the maximum water retention as defined by assuming that the carriers in the solid phase are deemed to be a single piece of carrier be at least 40 wt. % but at most 4,000 wt. %.

If a carrier does not by itself have any particular size like that made of a foamed organic high-molecular substance, it is only necessary to form the material into pieces of an appropriate size and to use them as many as needed.

In the present invention, spaces which exist in a carrier are called "voids" while spaces between pieces of the carrier are called "interstices".

No particular limitation is imposed on the microorganism used in the present invention insofar as it degrades a polymer. Eucaryotic microorganisms such as fungi and yeasts as well as procaryotic microorganisms such as bacteria and actinomycetes are usable. Also usable are microorganisms extracted from soil, microorganisms in activated sludge, and colonies in composts. Illustrative-bacteria include Pseudomonas bacteria, Escherichia bacteria and Bacillus bacteria. In addition, other bacteria are also included in a range of bacteria usable in the present invention insofar as they can degrade polymers.

As a microorganism suitably usable in the present invention, *Bacillus subtilis* MT-10658, a Bacillus sp. isolated from a soil by the present inventors, can be mentioned. Under the Budapest Treaty on microorganisms, this strain has been deposited under the deposition number of FERM BP-5341 (date of deposition: Dec. 19, 1995) with the National Institute of Bioscience and Human-Technology, Agency of Industrial Science and Technology, MITI, 1-3, Higashi 1-chome, Tsukuba-shi, Ibaraki-ken.

These microorganisms can be used singly. It is however not absolutely necessary to use them singly. Colonies of two or more microorganisms can be used preferably.

The term "nutrients" as used herein means substances required for the growth of a microorganism which degrades a polymer. No particular limitation is imposed insofar as a carbon source, a nitrogen source, inorganic salts and trace elements are contained. Bouillon medium (meat extract: 3 g/l, peptone: 10 g/l, sodium chloride: 5 g/l) can be mentioned by way of example.

As other components, it is also possible to incorporate components, which are contained in sewage sludge, urban garbage, livestock excrements or the like but cannot by themselves be used as a solid phase in the present invention, in the solid phase in such a way that the percentage of interstices of the whole solid phase does not fall below 25%. In some instances, a compost or the like is therefore also usable as a solid phase in the present invention.

According to the present invention, a carrier like that mentioned above is impregnated with an aqueous solution containing nutrients and a microorganism like a culture liquor. No particular limitation is imposed on the amount of the aqueous solution for the impregnation insofar as it is sufficient for the growth of the microorganism in the carrier and a space is left at such a level as permitting a supply of oxygen from the air. The amount of the solution is preferably at least 10% but at most 100%, more preferably at least 20% but at most 95%, still more preferably at least 25% but at most 90%, all based on the maximum water retention of the carrier.

The term "solid phase", which is employed to decompose a polymer in the present invention, means the entirety of a carrier, a microorganism, an aqueous solution containing nutrients required for the growth of the microorganism and water, and optional other components. If a solid phase is composed, for example, of pieces of a carrier impregnated with an aqueous solution containing a microorganism, nutrients and water, interstices should also be considered as a solid phase in the present invention, to say nothing of the carrier, the microorganism, the aqueous solution and voids.

Incidentally, the term "interstices" as used herein mean a whole space which remains after substantial portions of a carrier and other components are removed from a solid phase. In other words, the term "interstices" as used herein means a whole space which can accommodate a microorganism, nutrients, water and air, said nutrients, water and water being all required for the growth of the microorganism, in a solid phase. Accordingly, internal voids of pieces of a carrier, into which materials can penetrate, are also deemed as interstices, to say nothing of spaces or gaps between the pieces of the carrier.

The term "percentage of interstices" as used herein means the percentage of interstices based on the volume of a solid phase. If a carrier in a solid phase is made of a single material and contains no other component, the percentage of interstices is calculated in accordance with the following calculation formula 1:

[1−(apparent specific gravity/true specific gravity)]×100=percentage of interstices of the solid phase.    Calculation formula 1

In the present invention, the percentage of interstices of the solid phase is at least 25% but smaller than 100%, preferably at least 40%, more preferably 60% but smaller than 100%.

To practice the method of the present invention, it is only necessary to make pieces of a carrier and additional pieces of the carrier, the former pieces containing nutrients and the latter pieces being impregnated with an aqueous solution containing a microorganism, allow the microorganism to grow and then to bring a polymer, which is to be degraded, into contact with a container in which the carrier are contained, or to add the polymer into the container. The temperature at which the polymer is degraded is generally a temperature at which the microorganism is allowed to grow, and is specifically from 0 to 80° C., with 20 to 60° C. being preferred. Occasional mixing of the contents of the container may promote the degradation of the polymer. It is preferred to cause a gas to flow into the contents of the container.

It is also preferred to crush the polymer into appropriate dimensions upon bringing the polymer into contact with the solid phase, because the time required until degradation can be shortened.

Although the mechanism of degradation of the polymer by the method of the present invention has not been fully elucidated, enzymatic degradation by the microorganism itself, chemical hydrolysis of ester bonds of the polymer in the presence of ammonium ions or the like produced as a result of growth of the microorganism, or competitive occurrence of both may be contemplated. From the above viewpoint, it is therefore preferred to use, as nutrients for the present invention, a culture medium or the like which abundantly contains a nitrogen source, such as bouillon medium.

No particular limitation is imposed on the polymer subjected to degradation by the method of the present invention, insofar as it does not inhibit growth of the microorganism. Illustrative examples of the polymer include homopolymers or copolymers of hydroxycarboxylic acids such as lactic acid, glycolic acid, 6-hydroxycapronic acid, 3-hydroxybutyric acid and 3-hydroxyvaleric acid; and polyesters obtained from aliphatic dicarboxylic acids, such as succinic acid, adipic acid and cyclohexanedicarboxylic acids, and glycols such as ethylene glycol, 1,4-butanediol, 1,4-cyclohexanedimethanol and benzenedimethanol.

The method of the present invention can be suitably applied for the degradation of aliphatic polyesters, notably polymers formed from lactic acid, glycolic acid, or lactic acid and glycolic acid. The molecular weights of these aliphatic polyester polymers preferably range from 2,000 to 1,000,000.

Of these, a polylactic acid, especially poly(L-lactic acid) is particularly preferred.

No particular limitation is imposed on an apparatus which is usable in the present invention, insofar as it can practice the degrading method of the present invention and can degrade a polymer. The apparatus according to the present invention can be equipped with mixing means, aerating means, temperature control means and moisture control means as needed.

Figure 2:
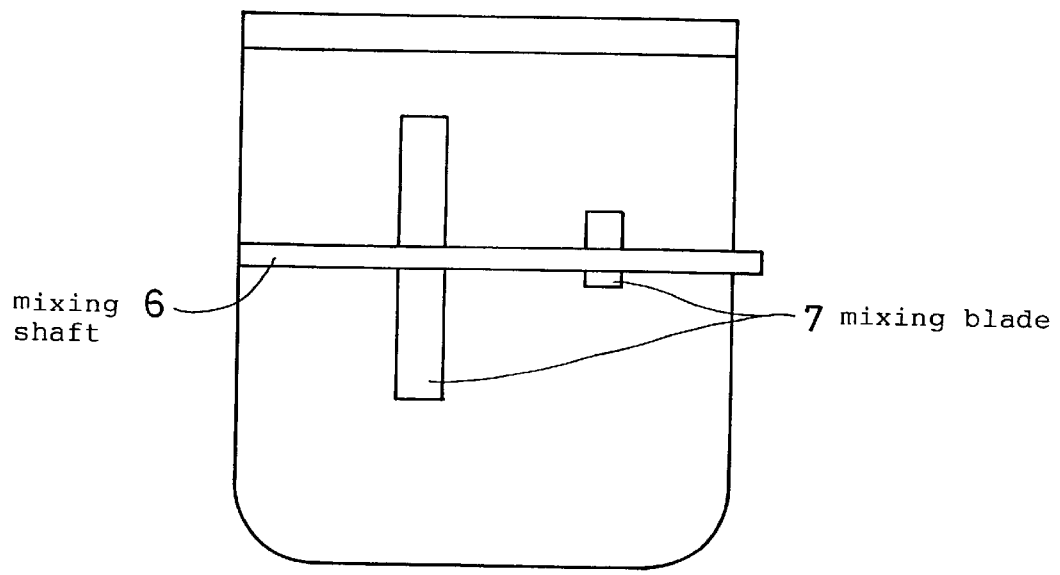

As one example of the apparatus according to the present invention, reference may be had to FIG. 1 and FIG. 2. As shown in FIG. 1, it is preferred to arrange a lower screen 3 in a bottom wall of a main body 1 and to form corner portions, which are defined between the bottom wall and respective side walls of the main body 1, into gently rounded or curved configurations. A top portion of the main body 1 is covered by a lid 2. An upper screen 4 is arranged in the lid 2. The lower screen 2 and the upper screen 4 both facilitate flows of gas and moisture through the main body. Aeration holes 5 may be formed as aerating means through one or more of the side walls of the main body. The main body 1 is provided with mixing means, which comprises a mixing shaft 6 and mixing blades 7. Rotation of the mixing shaft 6 by an electric motor or the like causes the mixing blades 7 to rotate, whereby the contents inside the main body are agitated. The shapes, number and positions of the mixing blades 7 can be modified as desired. Further, provision of means for incubating or cooling the main body 1 as a whole makes it possible to control the internal temperature of the main body.

EXAMPLES

The present invention will hereinafter be described specifically by the following examples. It should however be borne in mind that the present invention is by no means limited by or to the methods or scales to be described in the following examples.

Example 1

In each experiment, 20 g of one of the carriers shown in Table 1 were soaked with a sufficient amount of water and were then placed on a filter paper, whereby surplus water not held in the carrier was filtered off. The weight of the water-holding carrier on the filter paper was measured. The weight of the carrier was subtracted from the thus-measured weight to obtain a value as the weight of the held water, followed by the calculation of the maximum water retention of the carrier. The results are shown in Table 1.

In addition, the apparent specific gravity and true specific gravity of each carrier shown in Table 1 were also measured. Based on them, the percentage of interstices in a solid phase was calculated in accordance with the calculation formula 1. The results are also presented in Table 1.

In each experiment, 50 cm$^3$ of one of the carriers shown in Table 1 was placed in a 100-ml beaker. Further, each beaker was added with a culture medium of the composition, which is shown in Table 2, in an amount as much as 50 wt. % of the maximum water retention of the carrier, followed by steam sterilization at 120° C. for 30 minutes. After the sterilization, the carrier was cooled down to 37° C. and then inoculated with 1 ml of a culture liquor (about $10^8$ cells/ml) of *Bacillus subtilis* MT-10658, said culture liquor having been obtained by culturing the strain overnight in the culture medium of the composition shown in Table 2. A specimen film, which had been obtained from 1 g of poly(L-lactic acid) of about 100,000 in molecular weight by compression molding and had a size of 1×2 cm, was sterilized with 70% alcohol and inserted in the carrier. The carrier with the film inserted therein was maintained at 37° C. The progress of degradation of the specimen film was observed along the passage of time. The results are shown in Table 1. For the sake of comparison, Table 1 also shows the progresses of degradation of specimen films when clayey soil having a maximum water retention of 1,000 wt. % and a percentage of interstices of 20%, urethane pellets having a maximum water retention of 30 wt. % and a percentage of interstices of 60% and glass beads having a maximum water retention of 20 wt. % and a percentage of interstices of 35% were used as carriers, respectively, and when the microorganism was allowed to grow in the liquid culture medium shown in Table 2 without using any carrier and a specimen film was placed in the resulting culture liquor.

Incidentally, the term "degraded" in the table indicates that the specimen film became no longer visible (i.e., disappeared) in the course of the visual observation of the progress of degradation of the specimen film. A similar evaluation standard was used in the subsequent examples.

As a result of the experiments, the specimen films were all degraded when the solid phases having a maximum water retention of at least 40 wt. % (gramwater/gram-dry carrier) but at most 4,000 wt. % (gramwater/gram-dry carrier) and a percentage of interstices of at least 25% but smaller than 100% were employed. In contrast, the specimen films remained absolutely unchanged when the other carriers or solid phases were used. From this observation, the method of the present invention has been found to be effective for the degradation of the polymer.

Incidentally, employed as the saw dust and husks were those prepared by the inventors themselves prior to the experiments. Further, refined barley hulls (product of Takahashi Seifun K.K.) was used as the wheat bran; "FIBARM" (product of Sakai Engineering K.K.) as the porous foamed cellulose; urethane foam (product of Bridgestone Corporation) as the foamed urethane; "BELLEATER A" (product of Kanebo, Ltd.) as foamed polyvinyl alcohol; "Nonwoven fabric PLP" (product of Japan Vilene Co., Ltd.) as the non-woven fabric; "Molecular Sieve 3A" (product of Wako Pure Chemical Industries, Ltd.) as the molecular sieve; "Vermiculite Gold" (product of Sakata Seed Corporation) as the vermiculite; "Perlite M-1" (grain size: 1.5 mm to 3.0; product of Sakata Seed Corporation) as the perlite; "NASLON" (product of Nippon Seisen K.K.) as the stainless steel fibers; a solid collected in Mobarashi, Chiba-ken as the clayey soil; urethane pellets produced by Mitsui-Toatsu Chemicals, Inc. as the urethane pellets; and glass beads (average diameter: 2 mm; product of Iuchi Seieido K.K.) as the glass beads.

TABLE 1

| Carrier | Maximum water retention of carrier (%) | Percentage of interstices | Days until degradation |
| --- | --- | --- | --- |
| Saw dust | 140 | 60 | Degraded in 15 days |
| Husks | 220 | 60 | Degraded in 17 days |
| What bran | 290 | 70 | Degraded in 15 days |
| Porous foamed cellulose | 2630 | 98 | Degraded in 16 days |
| Foamed urethane | 1850 | 99 | Degraded in 15 days |
| Foamed PVC | 1300 | 88 | Degraded in 17 days |
| Nonwoven fabric | 800 | 98 | Degraded in 15 days |
| Molecular sieve | 70 | 60 | Degraded in 30 days |
| Vermiculite | 60 | 70 | Degraded in 19 days |
| Perlite | 300 | 70 | Degraded in 25 days |
| Stainless steel fibers | 700 | 90 | Degraded in 15 days |
| Clayey soil | 1000 | 20 | Unchanged over 90 days or longer |
| Urethane pellets | 30 | 60 | Unchanged over 90 days or longer |
| Glass beads | 20 | 35 | Unchanged over 90 days or longer |
| Without carrier (bouillon medium alone) | — | — | Unchanged over 90 days or longer |

TABLE 2

| (Bouillon Culture Medium) | |
| --- | --- |
| Meat extract | 3 g |
| Peptone | 10 g |
| Sodium chloride | 5 g |
| Distilled water | 1 l |
| pH | 7.0 |

Example 2

In portions of a culture medium of the composition shown in Table 2, the single-strain microorganisms shown in Table 3-1 to Table 3-3, i.e., *Escherichia coli* HB101 (commercially available), *Pseudomonas fluorescens* ATCC 13525 and *Bacillus subtilis* MT-10658 and as mixed-strain microorganisms, the standard activated sludge (Chemicals Inspection & Testing Institute, Japan) and soil extract microorganisms (collected from a soil in Mobara-shi, Chiba-ken) were separately cultured overnight. Further, the individual carriers shown in Table 3-1 to Table 3-3 were placed in 100-ml beakers in an amount of 50 cm$^3$ per beaker, respectively. Each of the carriers was added with the culture medium shown in Table 2 in an amount of 50 wt. % of the maximum water retention of the corresponding carrier, followed by steam sterilization at 120° C. for 30 minutes. The carrier was then allowed to cool down to 37° C., to which 1 ml of the above-described culture liquor (about $10^8$ cells/ml) was inoculated. A specimen film made of poly(L-lactic acid) having a molecular weight of about 100,000, which had been sterilized with 70% alcohol, was then inserted in the carrier. The carrier with the specimen film inserted therein was maintained at 37° C. The progress of degradation of the specimen film was observed over the passage of time. The results are shown in Table 3-1 to Table 3-3. For the sake of comparison, Table 3-1 to Table 3-3 also show the progresses of degradation of specimen films when the individual carriers were not inoculated with any microorganism, when clayey soil was used as a carrier, when the microorganisms were allowed to grow in the liquid culture medium shown in Table 2 without using any carrier and specimen film were placed in the resulting culture liquors, respectively. As a result of the experiments, the specimen films were degraded by various bacteria and mixed microorganisms, but no degradation took place when experiments were conducted without using any solid phase having, as a carrier, a maximum water retention of at least 40 wt. % (gram-water/gramdry carrier) but at most 4,000 wt. % (gram-water/gramdry carrier) and a percentage of interstices of at least 25% but smaller than 100% were employed.

TABLE 3-1

| | Inoculated microorganism | |
|---|---|---|
| Carrier | Not inoculated with microorganism | *Escherichia coli* |
| Saw dust | Unchanged over 90 days or longer | Degraded in 17 days |
| Husks | Unchanged over 90 days or longer | Degraded in 17 days |
| Wheat bran | Unchanged over 90 days or longer | Degraded in 17 days |
| Porous foamed cellulose | Unchanged over 90 days or longer | Degraded in 16 days |
| Foamed urethane | Unchanged over 90 days or longer | Degraded in 17 days |
| Foamed PVC | Unchanged over 90 days or longer | Degraded in 20 days |
| Nonwoven fabric | Unchanged over 90 days or longer | Degraded in 17 days |
| Molecular sieve | Unchanged over 90 days or longer | Degraded in 40 days |
| Vermiculite | Unchanged over 90 days or longer | Degraded in 32 days |
| Perlite | Unchanged over 90 days or longer | Degraded in 26 days |
| Clayey soil | Unchanged over 90 days or longer | Unchanged over 90 days or longer |
| Without carrier (medium alone) | Unchanged over 90 days or longer | Unchanged over 90 days or longer |

TABLE 3-2

| | Inoculated microorganism | |
|---|---|---|
| Carrier | *Pseudomonas fluorescens* | *Bacillus subtilis* |
| Saw dust | Degraded in 25 days | Degraded in 15 days |
| Husks | Degraded in 17 days | Degraded in 17 days |
| Wheat bran | Degraded in 23 days | Degraded in 15 days |
| Porous foamed cellulose | Degraded in 19 days | Degraded in 16 days |
| Foamed urethane | Degraded in 20 days | Degraded in 15 days |
| Foamed PVC | Degraded in 34 days | Degraded in 17 days |
| Nonwoven fabric | Degraded in 23 days | Degraded in 15 days |
| Molecular sieve | Degraded in 50 days | Degraded in 30 days |
| Vermiculite | Degraded in 37 days | Degraded in 19 days |
| Perlite | Degraded in 27 days | Degraded in 25 days |
| Clayey soil | Unchanged over 90 days or longer | Unchanged over 90 days or longer |
| Without carrier (medium alone) | Unchanged over 90 days or longer | Unchanged over 90 days or longer |

TABLE 3-3

| | Inoculated microorganism | |
|---|---|---|
| Carrier | Standard activated sludge | Soil extract microorganisms |
| Saw dust | Degraded in 27 days | Degraded in 31 days |
| Husks | Degraded in 25 days | Degraded in 33 days |
| Wheat bran | Degraded in 28 days | Degraded in 34 days |
| Porous foamed cellulose | Degraded in 21 days | Degraded in 25 days |
| Foamed urethane | Degraded in 22 days | Degraded in 27 days |
| Foamed PVC | Degraded in 42 days | Degraded in 45 days |
| Nonwoven fabric | Degraded in 31 days | Degraded in 35 days |
| Molecular sieve | Degraded in 70 days | Degraded in 80 days |
| Vermiculite | Degraded in 45 days | Degraded in 51 days |
| Perlite | Degraded in 47 days | Degraded in 55 days |
| Clayey soil | Unchanged over 90 days or longer | Unchanged over 90 days or longer |
| Without carrier (medium alone) | Unchanged over 90 days or longer | Unchanged over 90 days or longer |

Example 3

The single-strain microorganism, *Bacillus subtilis* MT-10658, shown in Table 4-1 to 4-2 was cultured overnight in a culture medium of the composition shown in Table 2. Further, the individual carriers shown in Table 4-1 to Table 4-2 were placed in 100-ml beakers in an amount of 50 cm$^3$ per beaker, respectively. Each of the carriers was added with the culture medium shown in Table 2 in an amount of 50 wt. % of the maximum water retention of the corresponding carrier, followed by steam sterilization at 120° C. for 30 minutes. The carrier was then allowed to cool down to 37° C., to which 1 ml of the above-described culture liquor (about 10$^8$ cells/ml) was inoculated. Specimen films (1×2 cm), one being made of a copolymer of poly(L-lactic acid) and polybutylene succinate and about 100,000 in molecular weight and the other being made of a homopolymer of polybutylene succinate and having a molecular weight of 100,000, which had been sterilized with 70% alcohol, were then inserted in the carrier. The carrier with the specimen films inserted therein was maintained at 37° C. The progress of degradation the two kinds of specimen films was observed along the passage of time. The results are shown in Table 4-1 to Table 4-2. For the sake of comparison, Table 4-1 to Table 4-2 also show the progresses of degradation of specimen films when the individual carriers were not inoculated with any microorganism, when clayey soil was used as a carrier, when the microorganisms were allowed to grow in the liquid culture medium shown in Table 2 without using any carrier and specimen films were placed in the resulting culture liquors, respectively. As a result of the experiments, the specimen films of the copolymer of poly(L-lactic acid) and polybutylene succinate and of the homopolymer of polybutylene succinate were degraded, but no degradation took place when experiments were conducted without using any solid phase having, as a carrier, a maximum water retention of at least 40 wt. % (gram-water/gram-dry carrier) but at most 4,000 wt. % (gram-water/gram-dry carrier) and a percentage of interstices of at least 25% but smaller than 100% were employed.

TABLE 4-1

| Carrier | Copolymer of poly (L-lactic acid) and polybutylene succinate | |
|---|---|---|
| | Not inoculated with microorganism | Inoculated with *Bacillus subtilis* |
| Saw dust | Unchanged over 90 days or longer | Degraded in 19 days |
| Husks | Unchanged over 90 days or longer | Degraded in 22 days |
| Wheat bran | Unchanged over 90 days or longer | Degraded in 20 days |
| Porous foamed cellulose | Unchanged over 90 days or longer | Degraded in 22 days |
| Foamed urethane | Unchanged over 90 days or longer | Degraded in 20 days |
| Foamed PVC | Unchanged over 90 days or longer | Degraded in 23 days |
| Nonwoven fabric | Unchanged over 90 days or longer | Degraded in 21 days |
| Molecular sieve | Unchanged over 90 days or longer | Degraded in 40 days |
| Vermiculite | Unchanged over 90 days or longer | Degraded in 26 days |
| Perlite | Unchanged over 90 days or longer | Degraded in 34 days |
| Clayey soil | Unchanged over 90 days or longer | Unchanged over 90 days or longer |
| Without carrier (medium alone) | Unchanged over 90 days or longer | Unchanged over 90 days or longer |

TABLE 4-2

| Carrier | Homopolymer of polybutylene succinate | |
|---|---|---|
| | Not inoculated with microorganism | Inoculated with *Bacillus subtilis* |
| Saw dust | Unchanged over 120 days or longer | Degraded in 55 days |
| Husks | Unchanged over 120 days or longer | Degraded in 65 days |
| Wheat bran | Unchanged over 120 days or longer | Degraded in 60 days |
| Porous foamed cellulose | Unchanged over 120 days or longer | Degraded in 65 days |
| Foamed urethane | Unchanged over 120 days or longer | Degraded in 61 days |
| Foamed PVC | Unchanged over 120 days or longer | Degraded in 68 days |
| Nonwoven fabric | Unchanged over 120 days or longer | Degraded in 61 days |
| Molecular sieve | Unchanged over 120 days or longer | Degraded in 100 days |
| Vermiculite | Unchanged over 120 days or longer | Degraded in 75 days |
| Perlite | Unchanged over 120 days or longer | Degraded in 90 days |
| Clayey soil | Unchanged over 120 days or longer | Unchanged over 120 days or longer |
| Without carrier (medium alone) | Unchanged over 120 days or longer | Unchanged over 120 days or longer |

Example 4

Under each of the conditions shown in Table 5, the corresponding raw materials were combined to form a personally-prepared compost. Composts so prepared were separately placed in 100-ml beakers in an amount of 50 cm³ per beaker. Each of the composts was adjusted so that the content of water and nutrients became 50% of the maximum water retention of the whole carrier.

In the compost under the condition A, the maximum water retention of the whole carrier contained in its solid phase was 250 wt. %, and the percentage of interstices in the solid phase was 60%.

In the compost under the condition B, the maximum water retention of the whole carrier contained in its solid phase was 220 wt. %, and the percentage of interstices in the solid phase was 60%.

In the compost under the condition C, the maximum water retention of the whole carrier contained in its solid phase was 220 wt. %, and the percentage of interstices in the solid phase was 50%.

In the compost under the condition D, the maximum water retention of the whole carrier contained in its solid phase was 140 wt. %, and the percentage of interstices in the solid phase was 60%.

In the compost under the condition E, the maximum water retention of the whole carrier contained in its solid phase was 220 wt. %, and the percentage of interstices in the solid phase was 20%.

A specimen film (1×2 cm), which was made of poly(L-lactic acid) having a molecular weight of about 100,000 and had been sterilized with 70% alcohol, was inserted in each compost, and the compost with specimen film inserted therein was maintained at 37° C. For the sake of comparison, to 50 cm³ of foamed urethane in a 100 ml-beaker, a culture medium of the composition shown in Table 2 was added in an amount of 50 wt. % of the maximum water retention of the foamed urethane, followed by steam sterilization at 120° C. for 30 minutes. The foamed urethane was allowed to cool down to 37° C., to which 1 ml of a culture liquor (about $10^8$ cells/ml) of *Bacillus subtilis* MT-10658, said culture liquor having been obtained by culturing the strain in the culture medium of the composition shown in Table 2, was inoculated. A specimen film of the poly(L-lactic acid) was then inserted in the thus-prepared foamed urethane. The carrier with the specimen film thus inserted was maintained at 37° C. The progress of degradation of the specimen film was observed along the passage of time. The results are shown in Table 6.

As a result of the experiments, the polymer was also found to degrade in the personally-prepared composts. Further, when the foamed urethane was used as a carrier, the specimen film degraded faster. The personally-prepared composts were experimented in view of composts available under the current situation, namely, composts which vary in quality (i.e., the carrier, initial nutrients, and the like) depending on the place or time of collection of each raw material. Substantial variations were observed in the gradation of the specimen films of poly(L-lactic acid).

TABLE 5

| Condition | Raw materials | Pre-culture period |
|---|---|---|
| A | Husks, dog food, human waste | 3 months |
| B | Husks, kitchen garbage, poultry manure, human waste | 3 months |
| C | Husks, kitchen garbage, poultry manure, human waste | 0 day |
| D | Saw dust, kitchen garbage, poultry manure, human waste | 3 months |

TABLE 5-continued

| Condition | Raw materials | Pre-culture period |
|---|---|---|
| E | Kitchen garbage, poultry manure, human waste | 0 day |

TABLE 6

| Condition | Days until degradation |
|---|---|
| A | Degraded in 60 ± 20 days |
| B | Degraded in 45 ± 14 days |
| C | Degraded in 25 ± 10 days |
| D | Degraded in 80 ± 25 days |
| E | Undegraded in 120 days |
| Foamed urethane | Degraded in 15 ± 2 days |

INDUSTRIAL APPLICABILITY

According to the method of the present invention, polymers having high strength at the time of use, especially polymers made form lactic acid, glycolic acid, or lactic acid and glycolic acid can be degraded promptly and surely. Further, a degrading disposal apparatus for polymers, which can promptly degrade the polymers by the method of the present invention, is also provided.

What is claimed is:

1. A method for degrading a polymer by bringing the polymer into contact with a solid phase composed of a carrier, a microorganism and an aqueous solution, said aqueous solution containing nutrients required for the growth of the microorganism and water, wherein said carrier has a maximum water retention of at least 40 wt. % but at most 4,000 wt. %, said aqueous solution is retained in said carrier in an amount of at least 10% but at most 100% of said maximum water retention of said carrier, and said solid phase has a percentage of interstices of 25% or greater but smaller than 100%.

2. The method of claim 1, wherein said polymer is a homopolymer or copolymer of a hydroxycarboxylic acid.

3. The method of claim 1, wherein said polymer is a polyester formed from an aliphatic dicarboxylic acid and a glycol.

4. The method of claim 3, wherein said carrier is made of an organic high-molecular substance or an inorganic substance.

5. The method of claim 4, wherein said organic high-molecular substance is a plant material, a non-human animal material, a foamed organic high-molecular substance or a fibrous organic high-molecular substance.

6. The method of claim 4, wherein said inorganic substance is a molecular sieve, vermiculite, perlite or stainless steel fibers.

7. The method of claim 3, wherein said microorganism is at least one bacterium selected from the group consisting of Pseudomonas bacteria, Escherichia bacteria and Bacillus bacteria.

8. The method of claim 7, wherein said microorganism is *Bacillus subtilis* FERM BP-5341.

9. An apparatus for degrading a polymer by bringing the polymer into contact with a solid phase composed of a carrier, a microorganism and an aqueous solution, said aqueous solution containing nutrients required for the growth of the microorganism and water, wherein said carrier has a maximum water retention of at least 40 wt. % but at most 4,000 wt. %, said aqueous solution is retained in said carrier in an amount of at least 10% but at most 100% of said maximum water retention of said carrier, and said solid phase has a percentage of interstices of 25% or greater but smaller than 100%.

10. The method of claim 2, wherein said carrier is made of an organic high-molecular substance or an inorganic substance.

11. The method of claim 1, wherein said carrier is made of an organic high-molecular substance or an inorganic substance.

12. The method of claim 10, wherein said organic high-molecular substance is a plant material, a non-human animal material, a foamed organic high-molecular substance or a fibrous organic high-molecular substance.

13. The method of claim 11, wherein said organic high-molecular substance is a plant material, a non-human animal material, a foamed organic high-molecular substance or a fibrous organic high-molecular substance.

14. The method of claim 10, wherein said inorganic substance is a molecular sieve, vermiculite, perlite or stainless steel fibers.

15. The method of claim 11, wherein said inorganic substance is a molecular sieve, vermiculite, perlite or stainless steel fibers.

16. The method of claim 2, wherein said microorganism is at least one bacterium selected from the group consisting of Pseudomonas bacteria, Escherichia bacteria and Bacillus bacteria.

17. The method of claim 1, wherein said microorganism is at least one bacterium selected from the group consisting of Pseudomonas bacteria, Escherichia bacteria and Bacillus bacteria.

18. The method of claim 16, wherein said microorganism is *Bacillus subtilis* FERM BP-5341.

19. The method of claim 17, wherein said microorganism is *Bacillus subtilis* FERM BP-5341.

\* \* \* \* \*